United States Patent [19]

Kline

[11] Patent Number: 5,024,600

[45] Date of Patent: Jun. 18, 1991

[54] PERIODONTAL SCALER-LIKE MEDICINAL FLUID APPLICATOR

[76] Inventor: Joseph M. Kline, 3501 N. Valley St., Arlington, Va. 22207

[21] Appl. No.: 470,791

[22] Filed: Jan. 26, 1990

[51] Int. Cl.⁵ .............................................. A61C 1/10
[52] U.S. Cl. .................................... 433/82; 433/143; 433/144
[58] Field of Search ................. 433/80, 82, 86, 119, 433/143, 144

[56] References Cited

U.S. PATENT DOCUMENTS

| | | | |
|---|---|---|---|
| 1,586,302 | 5/1926 | Funk | 433/80 |
| 2,818,647 | 1/1958 | Berliner | 433/143 |
| 3,368,280 | 2/1968 | Friedman et al. | 433/86 |
| 3,488,851 | 1/1970 | Haydu | 433/86 |
| 3,645,255 | 2/1972 | Robinson | 433/119 |
| 3,654,502 | 11/1972 | Carmona et al. | 433/119 |
| 4,332,558 | 6/1982 | Lustig | 433/86 |
| 4,370,131 | 1/1983 | Banko | 433/119 |
| 4,699,589 | 10/1987 | Friedman et al. | 433/80 |
| 4,854,867 | 8/1989 | Meinershagen | 433/143 |

FOREIGN PATENT DOCUMENTS

| | | | |
|---|---|---|---|
| 0015672 | 9/1980 | European Pat. Off. | 433/82 |
| 2566262 | 12/1985 | France | 433/119 |
| 2130099 | 5/1984 | United Kingdom | 433/143 |

Primary Examiner—Gene Mancene
Assistant Examiner—Michael Lynch
Attorney, Agent, or Firm—Dowell & Dowell

[57] ABSTRACT

A periodontal implement in form of a scaler or curette having at least one blade mounted to one end thereof in which the body of the implement includes at least one fluid passageway through which a source of medicinal fluid supply including germicidals, anesthetics, soothing agents hemostatics and the like are released to the area of the blade during patient treatment by controlled flow such as by metering or capillary action.

22 Claims, 2 Drawing Sheets

PERIODONTAL SCALER-LIKE MEDICINAL FLUID APPLICATOR

BACKGROUND OF THE INVENTION

1. Field of the Invention

This invention is generally directed to dental and periodontal implements and especially to medicinal fluid applicators in the form of scalers and curettes which include a source of fluid supply so that controlled amounts of the fluid may be directed to an area adjacent the cutting blade of such implements for purposes of applying medicinal fluids including germicidals, anesthetics, soothing agents and the like to the tissue adjacent the teeth being treated. The implements are supplied with a source of fluid through appropriate inlets or valves positioned within the handle of the implements. Each implement includes a channel through the shank which connects the blade to the handle of the implement through which the appropriate fluid may be dispensed in controlled amounts as the implement is manipulated with respect to the surface being treated. The medication is used before treatment, such as scaling, to reduce the infectious organisms present and possible further infection systemically. Also, the medication will reduce pain in the inflamed areas of all gum areas so as to make treatment less painful and reduce bleeding. Further applications may be made immediately after treatment, so the patient will have less pain for the next hour or so.

In some embodiments, the fluid may be supplied to the implement by way of separate meters which can be connected to the implement and which will regulate the quantity of fluid to within several 1/100ths of a milliliter or more. In other embodiments, the source of fluid supply will be a reservoir of about 1-3 quarts from which fluid is supplied through a conduit associated with a conventional dental fluid and air supply system. Such systems are subject to air pressure of up to about 35 pounds per square inch which pressure forces liquid through a conduit when an appropriate foot pedal operated control is activated. Fluid conveyed through the conduit or tubing is introduced either into one of two inlet ports in a double bladed instrument (single port in a single bladed instrument) or through an adjustable valve in an instrument handle which is selectively operated to direct fluid to one of the blade areas of a double bladed instrument. The valves and the openings and channels in the instruments may be of a specific size or dimension to regulate fluid flow from an instrument.

HISTORY OF THE RELATED ART

Heretofore there have been numerous dental and periodontal implements designed to supply a fluid to the area adjacent to the cutting or working ends thereof. In most instances, a source of cooling fluid is supplied through the implement handle and is discharged or directed across the shank which connects the handle to a cutting blade or drill so that the drill or cutting blade receives cooling fluid during the course of patient treatment. Such implements are normally ultrasonic or vibratory implements which have cutting surfaces or drills which are oscillated or rotated at very high speed rates so that the metallic surface of the cutting blades or drills will tend to heat up during use.

Unfortunately, the cooling of the blades of dental and periodontal implements, such as conventional fluid applicator scalers and curettes, does little to treat or soothe the tissue which surrounds the area or tooth being treated during scaling and other dental treatments. In fact, the continuous discharge of cooling fluid into a patient's mouth requires controlled aspiration of the injected fluid.

Scaling teeth with present day scalers and their sharp points is one of the more painful procedures in dentistry. Other than the injection of Novacaine or other anesthetics, which many people think is very painful, there is little that is being done other than swabbing the gums with a pleget of cotton to eliminate some pain on easy to reach outer gum surfaces.

As stated, it has been the accepted practice, in some cases, to treat a patient's gum tissue with individual sedative solutions using a cotton swab to apply the medication to the buccal and lingual surfaces, numbing agents, antiseptics, anesthetics, hemostatics and other fluids prior to periodontal treatment in order to reduce patient discomfort and in order to reduce the possibility of infection. However, such procedures require the necessary solutions be applied such as by swabbing the affected areas of the patient's mouth prior to treatment with a scaler or curette. Often, however, the time of the scaling or curetting treatment may exceed the effective life of the agent applied. Also, surface application of such treatment solutions does not provide for application of the solutions to areas between teeth or to the area of the periodontal pockets in which scaling and curettaging is being, or is to be, performed. Therefore, to date, there have been no comprehensive effective means to supply antiseptics, numbing agents, anesthetics, hemostatic and other medicinal fluids to the deep periodontal pocket areas below the gum line and between teeth of a patient's mouth to both reduce patient discomfort as well as to control the possible exposure of both the patient and the practitioner to bacteria.

Some examples of prior art dental equipment which incorporate fluid sprays include U.S. Pat. No. 3,368,280 to Friedman et al., U.S. Pat. No. 3,488,851 to Haydn, U.S. Pat. No. 4,332,558 to Lustig, and U.S. Pat. No. 4,699,589 to Friedman et al. as well as European Patent Application 0015672, filed Dec. 2, 1980.

SUMMARY OF THE INVENTION

This invention is generally directed to dental and periodontal implements similar to scalers and curettes and more particularly to such implements which include a source of medicinal fluid supply which is introduced to an area adjacent the blades of such implements by way of passageways provided through the shanks which connects the implement handles to the blades. In some instances the implement may be connected through suitable valves to a metering device or pump which will supply medicinal fluids to a passageway within the implement handle so that metered amounts of liquid may be conveyed to the area adjacent the blades during patient treatment.

The implements are provided with fluid from a fluid reservoir which may be associated with a conventional dental fluid and air system. In this embodiment, each fluid applicator will be provided with fluid passageways which communicate with each of the blades and which are either in fluid communication with separate inlet ports which extend outwardly of the instrument handle or with a selector valve which may be selectively aligned with one of the passageways and which may be connected to a suitable delivery tube or conduit. In either case, the medicinal fluid is conveyed from the fluid reservior, which may be a pressurized tank having a capacity of up to several quarts, upon selective activation of the pressure supply by a control such as a conventional foot pedal.

In either embodiment of the invention, the upper surface of the blades of the implements may be recessed or grooved to provide a trough through which fluid being discharged through an opening provided in the shank of the instrument adjacent the cutting blade may be conveyed. The blades may also include one or more openings therethrough which will channel the fluid through and to the lower surface of the blades so that medicinal fluids may be supplied to areas, such as deep periodontal pockets, below the blades. Additionally, the edges of the implements may include a series of spaced grooves which will communicate with the recessed upper surface to thereby permit fluid to seep laterally of the blade. Also, to prevent tissue irritation, the outer edges of the blades are rounded or dull.

It is the primary object of the present invention to provide a dental or periodontal fluid applicator instrument having blades in the general configuration of a scaler or curette which will provide controlled release of medicinal fluids to the tissue area adjacent a tooth either before, during or after dental treatments including scaling or curettaging to thereby apply medicine, numbing agents, disinfectants, hemostatics or other fluids to the periodontal pocket below the gumline or to areas between teeth.

It is another object of the present invention to provide a dental implement or periodontal implement in which medicinal fluids including numbing agents, antiseptics, cleaning agents, bacteriacides, anesthetics, soothing and the like may be applied to a patient's gum with the amount of the agent being controlled either or both by the movement of the implement relative to the treated area by discharge of the fluid by capillary action from the implement as the blade of the instrument passes into the gingival crevices or pockets adjacent to the teeth of a patient's mouth and with suitable pressure regulation.

It is yet a further object of the present invention to provide a dental or periodontal implement wherein a variety of medicinal fluids may be applied by the implement to areas between teeth and to deep periodontal pockets mesial and distal, buccal and lingual, and bifurcations of roots to thereby reduce patient discomfort and bleeding, alleviate pain, and achieve increased curative effects by permitting the deep application of fluids which will destroy bacteria and prevent disease transmission and systemically reduce pain.

DESCRIPTION OF THE PREFERRED EMBODIMENT

Figure 1:
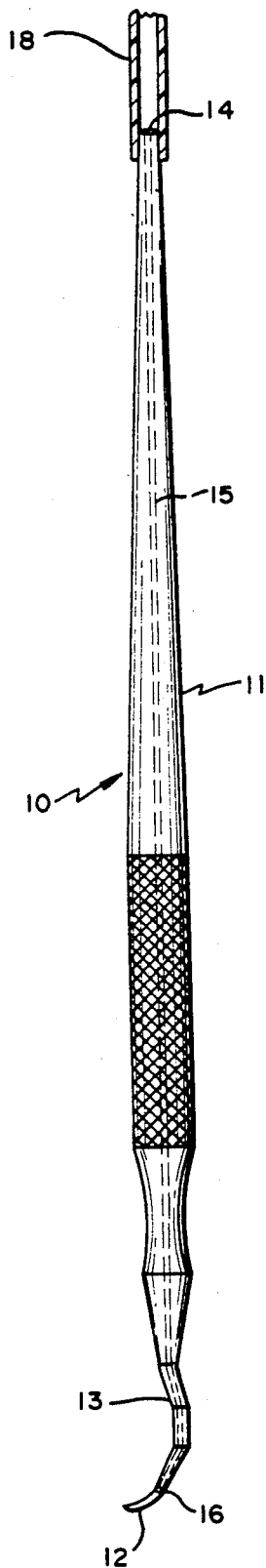
FIG. 1 is a side elevational view of a first embodiment of the present invention showing a scaler-like dental instrument for introducing fluid into areas between teeth and into periodontal pockets.

With continued reference to the drawings, the first embodiment of the present invention is shown in FIG. 1. In this embodiment, the medicinal applicator scaler-like instrument 10 is shown as having a handle 11 which is connected to a blade-like element 12 by way of a shank 13. The shank and blade orientation shown in the figures is generally similar to the configuration of a GRACEY 13-14 posterior implement and may be used along mesial and distal anterior and posterior teeth of the patient. The exact configuration and orientation of the shank and of the blade-like elements may change if desired, although the straight blade configuration associated with GRACEY 13-14 implements is preferred so that a single instrument can be used for anterior and posterior, mesial, distal and buccal and lingual areas to be treated.

The handle 11 includes an opening 14 adjacent the uppermost end thereof which opening communicates with a fluid passageway 15 which extends along the length of the instrument and through the shank 13. The fluid passageway communicates at the shank end of the instrument with an opening 16 which is positioned adjacent to the blade element 12. Medicinal fluid is provided to the instrument by way of a fluid tube or conduit 18 in a manner which will be described in greater detail hereinafter.

In the use of the instrument disclosed in FIG. 1, the medicinal fluid supplied to the instrument by way of the tubing 18 may be regulated by a separate metering device not shown. Further, the size of the channel 15 can be utilized to regulate the rate of fluid flow and therefore the size of the channel may vary from one instrument to another. The opening 16 is positioned so as to direct fluid passing from the channel 15 onto the upper surface of the blade element 12. From the blade, the medicinal fluid will be directed to areas between a patient's teeth and in areas below the gumline and deep periodontal pockets which areas were previously not accessible by conventional medicinal swab type applicators.

Figure 2:
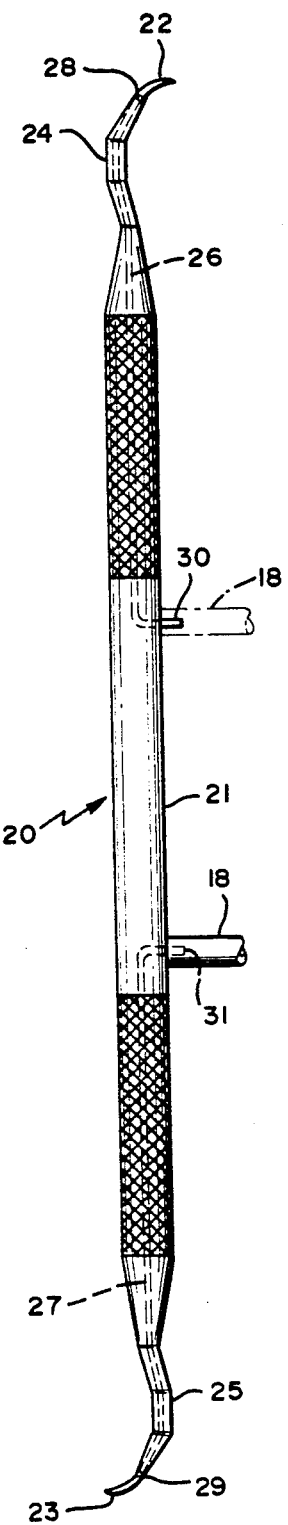
FIG. 2 is a side elevational view of a second embodiment of the present invention showing a scaler-like dental instrument for introducing medication into areas between teeth and into periodontal pockets wherein the medication may be applied through either end of the instrument.

With reference to FIG. 2 of the drawings, a second embodiment of the present invention is disclosed in greater detail. In this embodiment, the medicinal applicator scaler-like instrument 20 is shown as including a handle 21 having opposite blade elements 22 and 23 mounted thereto by way of arcuately formed shanks 24 and 25. In this embodiment, medicinal fluid may be applied from either end of the instrument and therefore the instrument is provided with a pair of fluid passageways designated as 26 and 27 with fluid passageway 26 communicating with blade element 22 by way of opening 28 and with fluid passageway 27 communicating with blade element 23 by way of fluid opening 29. The size of the fluid passageways 26 and 27 and the openings 28 and 29 may be regulated to control the flow of fluid as was discussed above with respect to the embodiment of FIG. 1. In addition, fluid being discharged through the openings 28 and 29 to the blade elements 22 and 23 will be deposited along the upper surface of the blade elements and will be discharged therefrom in a manner to be discussed in greater detail hereinafter.

In order to supply fluid to the passageways 26 and 27, a pair of inlet ports 30 and 31 are provided. Inlet port 30 communicates with fluid passageway 26 and inlet port 31 communicates with fluid passageway 27. The fluid ports are of a size, at least ¼ inch in length, to selectively receive the medicinal supply tubing or conduit 18.

The medicinal applicator instrument 20 is designed so that one of the blade elements may be utilized on buccal mesial-distal surfaces between two teeth while the other end is used on lingual mesial-distal surfaces or areas of a patient's teeth.

Figure 3:
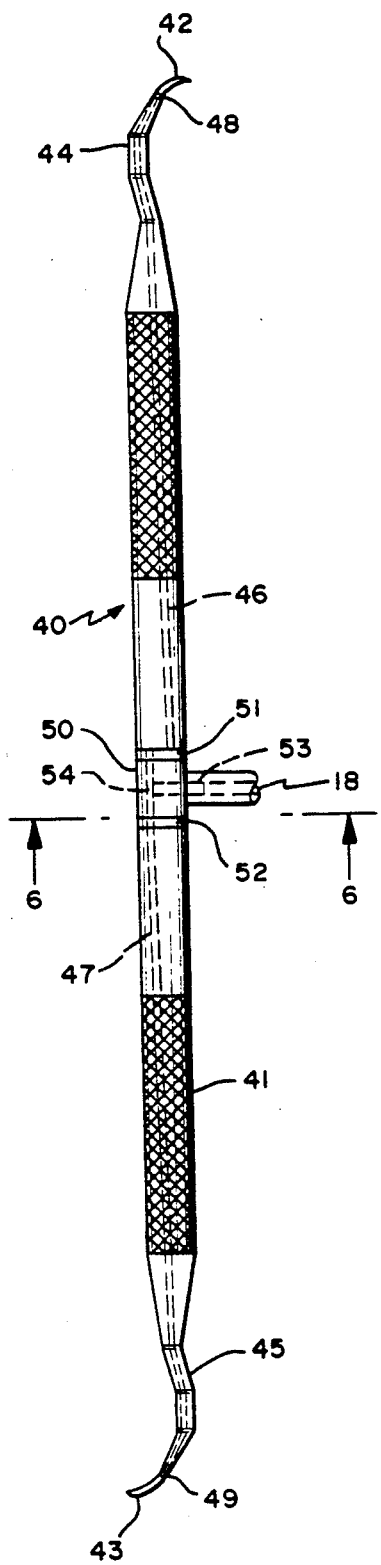
FIG. 3 is a side elevational view of a third embodiment of the present invention which incorporates a valve for selectively introducing fluid to either end of the dental instrument.

With reference to FIG. 3, a modification of the embodiment shown in FIG. 2 is disclosed in greater detail. In this embodiment, the instrument 40 includes a handle 41 to which are mounted blade elements 42 and 43 by way of shanks 44 and 45. Also, as was the case with the embodiment of FIG. 2, one of the blade elements 42 or 43 is designed for use on buccal mesial-distal surface areas while the opposite blade is designed for use on lingual mesial-distal surface areas between two teeth.

The instrument 40 includes a pair of fluid passageways 46 and 47 with fluid passageway 46 communicating with the blade element 42 by way of an opening 48 formed in the end of the shank 44 adjacent to blade 42. Fluid passageway 47 communicates with blade element 43 by way of an opening 49 provided in the lower end of the shank 45. As shown, the fluid passageways 46 and 47 are offset with respect to one another within the handle 41. A rotary selector valve 50 is mounted in spaced bearings 51 and 52. Bearing 51 has an opening therethrough which aligns with fluid passageway 46 while bearing element 52 has an opening therethrough which aligns with fluid passageway 47.

Figure 6:
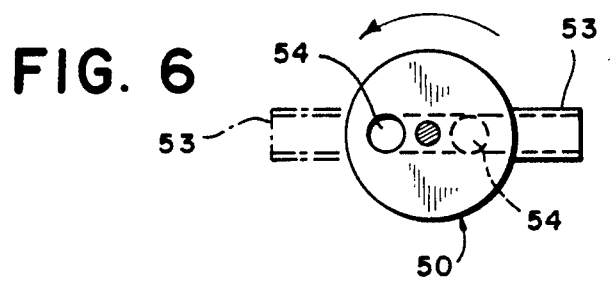
FIG. 6 is an enlarged cross sectional view taken along lines 6—6 of FIG. 3.

The selector valve 50 includes an inlet port 53 which extends outwardly with respect to the handle and to which the medicinal supply tube 18 may be selectively secured. The valve further includes a T-shaped fluid passageway 54 which may be selectively aligned with either of the fluid passageways 46 and 47 as the upper portion of the T passageway is offset with respect to the axis of rotation of the valve 50. In the position shown in FIG. 3, the valve passage 54 is aligned with fluid passage way 47 so that fluid entering through port 53 will be directed to the outlet opening 49 adjacent to the blade 43. By simple rotation of the valve in a plane perpendicular to the elongated axis of the handle the valve passageway 54 will be aligned with fluid passageway 46. The operation of the valve is shown in greater detail in FIG. 6. In FIG. 6, the valve is shown in full line as being in the position shown in FIG. 3 and in dotted line in a position to align with fluid passageway 46 of the implement 40 to thereby direct fluid through the opening 48 and to the blade element 42.

Figure 5:
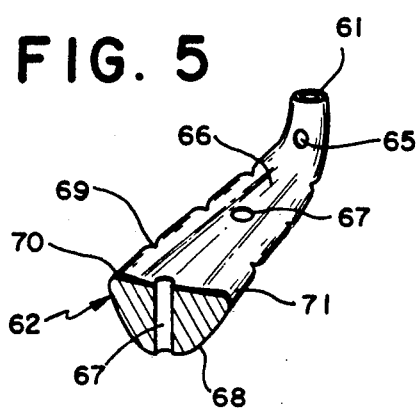
FIG. 5 is an enlarged perspective cross sectional view of the blade-like element of FIG. 4.
Figure 4:
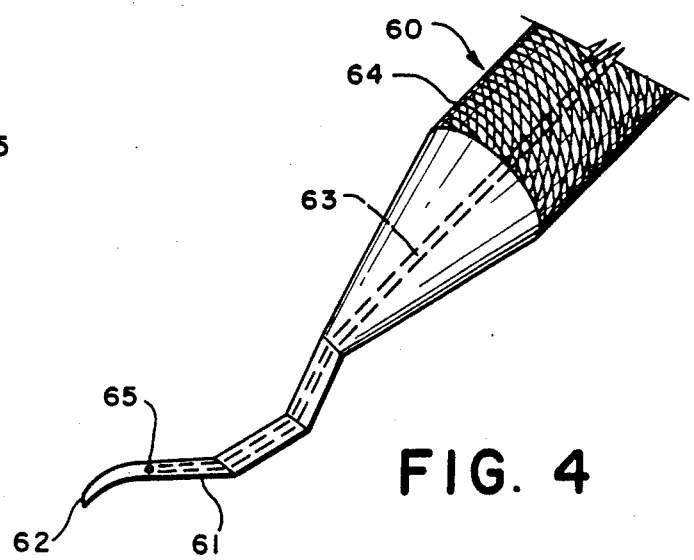
FIG. 4 is an enlarged perspective end view of one of the blade-like elements of the dental implement of the present invention.

With specific reference to FIGS. 4 and 5, the blade elements of the present invention are disclosed in greater detail. As previously discussed, the blades of the present invention are designed in the general configuration of a small conventional fine scaling blades so that the blade elements may be utilized to introduce fluid between teeth, below the gumline, buccal and lingual, in root bifurcation areas and in deep periodontal pockets. Due to the straight blade configuration of posterior scalers of the GRACEY 13-14 type, such configurations are preferred for the purposes of the present invention. However, in the preferred embodiment the blade elements, themselves, are slightly different in configuration as it is intended that the blade elements introduce medicinal fluid to the tissues surrounding an area to be treated before and after scaling or curetting and sometimes during treatment.

In FIG. 4, one end of a medicinal applicator, scaler-like, implement 60 is disclosed which has a structure similar to that of the instrument 40 shown in FIG. 3 and includes a shank 61. A blade 62 is shown as extending from the outermost portion of the shank 61. Fluid is supplied to the blade element 62 by way of a fluid passageway 63 which extends through the implement handle 64 and the shank 61. The passageway 63 communicates with an opening 65 in the lower end of the shank 61.

As shown more specifically in FIG. 5, fluid from the opening 65 is directed onto the upper surface 66 of the blade 62. The upper surface is shown as being recessed or somewhat concave in configuration so that as the fluid exits from the opening 65, it will be directed along the upper face of the blade. The blade further includes a plurality of openings 67 therethrough by way of which fluid may be channeled from the upper face 66 to the lower surface 68 of the blade. To further assist in the distribution of medicinal fluid from the upper surface of the blade, a series of small recesses 69 may be provided along the edges 70 and 71 of the blade. Further, it should be noted that the edges 70 and 71 are rounded so as not to irritate tissue as the implement is inserted in areas between a patient,s teeth and gums and into gingival pockets.

The openings 67 in the blade element 62 permit drainage of medicinal fluid to the lower surface or base of the blade. Thus, when the blade is inserted into a pocket next to the root surface these openings or holes allow air or fluids to escape and permit easier insertion of the implement Further, when fluid is being introduced to the upper surface of the blade after the blade has been inserted into a periodontal pocket, the lifting of the blade relative to the pocket will create a suction which will draw the fluid through the openings thereby to saturate and medicate the area adjacent to and under the blade This procedure is continued around all the teeth and in the gum areas where any dental treatment is contemplated.

Figure 7:
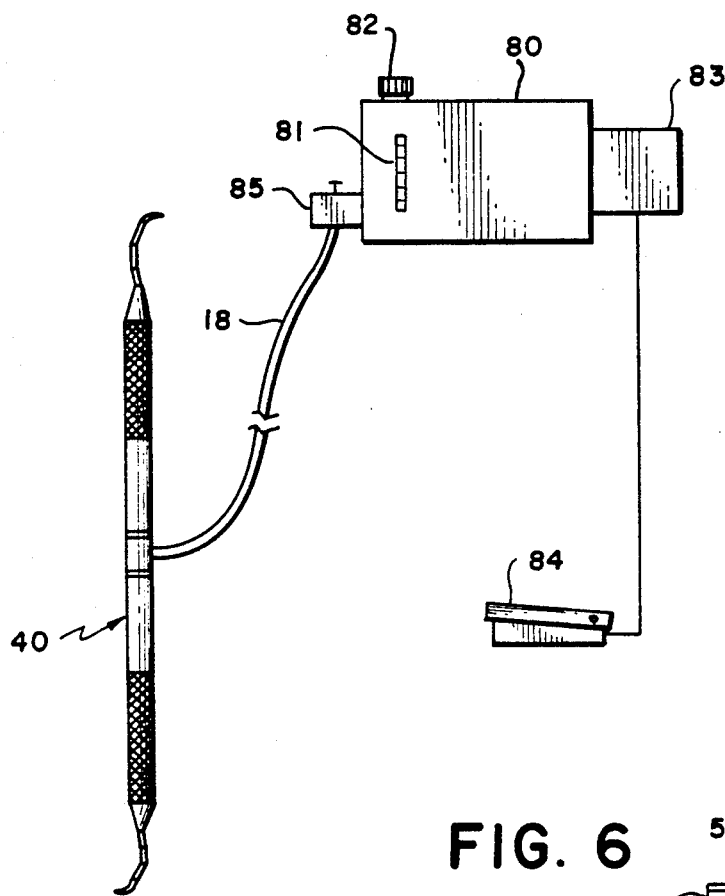
FIG. 7 is an illustrational view of the embodiment shown in FIG. 3 being connected to a source of medicinal supply.

With specific reference to FIG. 7, one source of supplying medicinal fluids to the medicinal applicators of the present invention is shown in greater detail. In this Figure, the fluid supply source is shown as being connected to an instrument similar to that as shown at 40 in FIG. 3. The source of fluid supply includes a tank or container 80 which may be of a size to hold one or more quarts of medicinal fluid. The container is provided with a volume indicating scale 81 so that the amount of fluid remaining within the container may be easily discerned. Additional fluid may be added to the container via an inlet 82 provided in the upper surface thereof. Fluid from the container 80 is provided under pressure to the fluid supply tubing or conduit 18 by activating a source of pressure 83 by way of a foot control element 84 which may be of a type which is conventionally utilized with liquid and air supply equipment associated with conventional dental instruments. In this manner, the practitioner may selectively activate the fluid supply source by way of the foot control to thereby selectively administer medicinal fluids to the instrument 40. A metering valve 85 may be incorporated with the fluid supply source to thereby also selectively regulate the fluid flow rate.

A variety of medicinal fluids may be applied in combination utilizing implements of the present invention, some conventional treating agents include xylocaine or benzocaine which are utilized as an anesthetizing agent; various phenol agents which are utilized as antiseptics; aconite which is used as a soothing agent; thrombin topical which is a hemostatic; iodine which is utilized as an antiseptic agent; and glycerines and alcohols which are utilized as medicinal carriers or vehicles. Hemostatic medications are present in many medications such as Hemodent. Other generic drugs can be provided to retard bacteria. The phenols and iodine solutions are hemostatic as well as bacteriostatic. Also, different combinations of these and newer medications can be formulated. The application of medicinal materials can also be used before cavities exist below the gum on any surface to function in many ways for a patient's benefit and the benefit to dentistry.

Although the implements of the invention have been defined as being used with "scaler-like" or "curette-like" implements, it is envisioned that the implements could, in somes instances, include cutting blades and be functional as scalers and curettes.

I claim:

1. A periodontal implement for applying a medicinal fluid to the tissue in a patient's mouth adjacent teeth to be treated comprising, a handle having a first blade extending therefrom, a first shank for connecting said first blade to said handle, a first fluid passageway within said handle, said first fluid passageway extending within said first shank, a first opening in said first shank which communicates with said first fluid passageway, said first blade having an upper and lower surface, said upper surface having a recess formed therein for receiving fluid from said first opening, and said first blade including at least one opening therethrough extending from said upper surface to the lower surface thereof.

2. The periodontal implement of claim 1 in which said handle has an end opposite said first blade, an opening in said opposite end which communicates with said first fluid passageway.

3. The periodontal implement of claim 2 including a fluid reservoir, conduit means connecting said fluid reservoir with said opposite end of said handle, and means for discharging fluid from said fluid reservoir through said conduit means and into the implement.

4. The periodontal implement of claim 1 in which said first blade includes opposite edge portions, said edge portions being rounded.

5. The periodontal implement of claim 4 including a plurality of grooves formed in said edge portions of said first blade.

6. The periodontal implement of claim 1 in which said handle includes opposite ends, said first blade extending outwardly from one of said ends, a second blade extending outwardly from the opposite end of said handle, a second shank for connecting said second blade to said handle, a second fluid passageway extending through said handle and said second shank, a second opening in said second shank communicating with said second fluid passageway and fluid inlet means for supplying a source of fluid to said first and second fluid passageways.

7. The periodontal implement of claim 6 in which said means for supplying fluid includes a first inlet port in fluid communication with said first fluid passageway and a second inlet port spaced from said first inlet port and communicating with said second fluid passageway.

8. The periodontal implement of claim 7 in which said second blade includes upper and lower surfaces, said upper surface being generally recessed, and said second opening being oriented so as to discharge fluid to said recess in said upper surface.

9. The periodontal implement of claim 8 in which said second blade includes at least one opening therethrough between said upper and lower surfaces thereof.

10. The periodontal implement of claim 9 in which said second blade includes outer edge portions, said outer edge portions being generally rounded.

11. The periodontal implements of claim 10 including grooves formed in said outer edge portions of said second blade.

12. The periodontal implement of claim 7 in which said means for supplying a source of fluid includes a fluid conduit selectively connected to one of said first and second inlet ports, a fluid reservoir, and means for applying pressure to said fluid reservoir so as to discharge fluid therefrom and through said conduit into the implement by way of said first or second ports.

13. A periodontal implement for applying a medicinal fluid to the tissue in a patient's mouth adjacent teeth to be treated comprising, a handle having opposite ends, a first blade extending outwardly from one of said ends, a second blade extending outwardly from the opposite end of said handle, a first shank for connecting said first blade to said handle, a second shank for connecting said second blade to said handle, a first fluid passageway within said handle, said first fluid passageway extending through said handle and said first shank, a first opening in said first shank which communicates with said first fluid passageway, said first opening being oriented so as to discharge fluid to said first blade, a second fluid passageway extending through said handle and said second shank, a second opening in said second shank communicating with said second fluid passageway, fluid inlet means for supplying a source of fluid to said first and second fluid passageways, said means for supplying fluid includes a valve means mounted within said handle, said valve means being rotateable between a first and a second position and including an inlet and an outlet passageway, said outlet passageway of said valve means communicating with said first fluid passageway when in said first position and communicating with said second fluid passageway when in said second position.

14. The periodontal implement of claim 13 in which said first and second blades include upper and lower surfaces, said upper surface being generally concave.

15. The periodontal implement of claim 14 in which said first and second blades have at least one opening therethrough between said upper and lower surfaces.

16. The periodontal implement of claim 15 in which said first and second blades include outer edges, said outer edges being generally rounded.

17. The periodontal implement of claim 16 including grooves in said outer edges of said first and second blades.

18. The periodontal implement of claim 13 in which said means for supplying a source of fluid also includes a fluid conduit selectively connected to said inlet of said valve, a fluid reservoir, and means for applying pressure to said fluid reservoir so as to discharge fluid therefrom and through said conduit into the implement by way of said valve.

19. A periodontal implement for applying a medicinal fluid to the tissue in a patient's mouth adjacent teeth to be treated comprising, a handle having at least one blade extending therefrom, a shank for connecting said blade to said handle, a fluid passageway within said handle, said fluid passageway extending within said shank, an opening in said shank which communicates with said fluid passageway, said opening being oriented so as to discharge fluid to said blade, said blade having opposite edge portions, and a plurality of grooves formed in said edge portions of said blade.

20. The periodontal implement of claim 19 in which said edge portions of said blade are rounded.

21. The periodontal implement of claim 19 in which said blade includes upper and lower surfaces, said upper surface having a recess formed therein for receiving fluid from said first opening.

22. The periodontal implement of claim 21 in which said blade includes at least one opening therethrough extending from said upper surface to the lower surfaces thereof.

* * * * *